United States Patent [19]

Shander

[11] Patent Number: 4,720,489

[45] Date of Patent: Jan. 19, 1988

[54] HAIR GROWTH MODIFICATION WITH ORNITHINE DECARBOXYLASE INHIBITORS

[76] Inventor: Douglas Shander, 5 Meadowgrass Ct., Gaithersburg, Md. 20878

[21] Appl. No.: 661,019

[22] Filed: Oct. 15, 1984

[51] Int. Cl.$^4$ .................. A61K 31/56; A61K 31/13; A61K 31/195

[52] U.S. Cl. .................. 514/171; 514/667; 514/671; 514/564

[58] Field of Search ............ 260/397.4; 424/241; 514/178, 180, 171, 564, 667, 671

[56] References Cited

U.S. PATENT DOCUMENTS 4,456,586  6/1984  Van ler Berghe et al. .. 260/239.5 SR
4,457,925  7/1984  Bittler et al. .............. 260/239.5 SC

OTHER PUBLICATIONS

Chemical Abstracts, vol. 100 (1984), #172302z, Ogawa et al.
Fed. Register, vol. 45, No. 218, dated Nov. 7, 1980.
Fed. Register, vol. 50, No. 10, dated Jan. 15, 1985.

*Primary Examiner*—Leonard Schenkman
*Assistant Examiner*—Joseph A. Lipovsky
*Attorney, Agent, or Firm*—Mandel E. Slater

[57] ABSTRACT

The rate and character of human hair growth including androgen-stimulated beard hair growth in intact, sexually mature males is altered by the topical application out of a dermatologically acceptable carrier of a material capable of inhibiting the action of the enzyme ornithine decarboxylase. In a preferred practice of the invention, compositions containing such materials along with anti-androgen material are employed.

9 Claims, No Drawings

HAIR GROWTH MODIFICATION WITH ORNITHINE DECARBOXYLASE INHIBITORS

This invention relates to a new and novel approach in the reduction of the rate and alteration of the character of human hair growth by the topical application of compositions containing materials capable of inhibiting the action of the enzyme ornithine decarboxylase in its role in the proliferative activity of hair follicle matrix cells.

BACKGROUND OF THE INVENTION

The decarboxylation of ornithine to putrescine, a reaction catalyzed by the enzyme ornithine decarboxylase (OCD), is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-Adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in embryonic tissue; in the testes, ventral prostrate, and thymus; in tumor tissue; in psoriatic skin lesions; and in other cells undergoing rapid growth or proliferation.

Since putrescine is the precursor of both spermidine and spermine, blockade of the conversion of ornithine to putrescine, such as by inhibition of ODC, should prevent new biosynthesis of these polyamines and, thus, provide beneficial physiological effects.

Much of the medical investigation which has been directed to the elucidation of the mechanism of hair growth has focused on the role of the endocrine system. As a result of such investigations, it is generally agreed that the fine, light-colored vellus hair, which covers most of the body during childhood, comes under the influence of growth hormone and of androgens to eventually become the coarser and darker terminal hairs which characterize many areas of the adult body. The desire to discover methods for controlling androgen-dependent conditions has generated a large number of studies dealing with androgen metabolism in skin. These studies have suggested that it is possible to reduce the amount of androgen capable of entering into the hair growth cycle by two means.

Firstly, the conversion of serum testosterone to dihydrotestosterone can be prevented by the inhibition of the enzyme steroid 5-alpha-reductase. Secondly, certain compounds can compete with the testosterone or dihydrotestosterone for the cytoplasmic receptor sites. The action of both types of antiandrogen compounds in skin can also affect the course of male-pattern hair growth in females, thus leading to their application in the treatment of female hirsutism. Such application is described, inter alia, in the following patents:

U.S. Pat. Nos. 4,139,638 and 4,151,540 describe the use of certain 4'-substituted and 3', 4'-disubstituted anilides for the treatment of androgen-dependent disease states such as female hirsutism and acne.

U.S. Pat. No. 4,191,775 discloses that certain 3,4-disubstituted-branched-chain-fluorinated-acylanilides may be used in the topical treatment of androgen-dependent disease conditions such as acne, female hirsutism, and seborrhoea.

U.S. Pat. No. 4,344,943 describes the topical use of certain androgenic 17-alpha-substituted steroids exemplified by 17-beta-hydroxyl-1-alpha-methyl-17-alpha-(1-methyl-2-propenyl)-5-alpha-androstan-3-one for the treatment of diseases such as acne, seborrhoea, alopecia and female hirsutism.

West German OLS No. 2,840,144 describes the use of combinations of progesterone with either cyproterone acetate or chlormadinone acetate in the topical treatment of androgen-induced hormonal disturbances such as alopecia, female hirsutism, and acne.

The patent art also discloses a number of non-steroidal methods of reducing the growth of human hair as opposed to its conventional removal by cutting, shaving, or depilation. One such method is described in U.S. Pat. No. 3,426,137, which pertains to a process for inhibiting the growth of hair by the topical application to a depilated skin area of a composition containing a substituted benzophenone such as 2-amino-5-chlorobenzophenone. Examples in the patent illustrate the reduction of hair growth on the back area of rabbits and on the arm of a male human subject.

Another process for extending the duration of depilation is described in U.S. Pat. No. 4,370,315. The process therein comprises the topical application of a composition containing a lipoxygenase along with linoleic acid or derivative thereof. The patent describes the application of such composition to various body parts of female subjects in the majority of which regrowth of hair was clearly perceptible only after six or more weeks.

Ornithine decarboxylase was essentially unknown until the late 1960's. This enzyme remained in a state of relative obscurity until it was realized that its activity is the rate-determining step in the biosynthesis of polyamines which are produced by mammalian species. The application of this discovery has led to the administration of ODC inhibitors in the treatment of a variety of conditions. Prior art references describing such applications include, inter alia:

U.S. Pat. No. 4,413,141 relating to 2-difluoromethyl(-2,5-diaminopentanoic) acid or its salts as contra-gestational agents, for use in the treatment of benign prostatic hypertrophy, for use in slowing neoplastic cell proliferation and as an anti-protozoal agent.

U.S. Pat. No. 4,421,768 dealing with fluorinated diamino-heptene and -heptyne derivatives for use in controlling the growth rate of rapidly proliferating tumor tissue and for controlling the growth of pathogenic parasitic protozoa.

U.S. Pat. No. 4,207,315 claiming a process for treating non-malignant proliferative skin disease by the application of diamines of aliphatic hydrocarbons or derivatives of ornithine in association with a pharmaceutical carrier.

U.S. Pat. No. 4,201,788 claiming a process for treating nonmalignant proliferative skin diseases by the administration of a compound exemplified by methyl glyoxal bis-(guanyl hydrazone) in association with a pharmaceutical carrier.

SUMMARY OF THE INVENTION

I have discovered that a wide variety of inhibitors of ornithine decarboxylase activity (ODC inhibitors) may be employed in altering the rate and character of human hair growth including androgen-stimulated hair growth in the beards of intact, sexually mature males. The ODC inhibitors are applied topically out of a dermatologically acceptable carrier for local effect with minimal alteration of other bodily functions through systemic action. In a preferred practice of the invention, there are employed compositions containing ODC inhibitors along with 5-alpha-reductase inhibitors and/or cytoplasmic receptor-binding agents.

DETAILED DESCRIPTION OF THE INVENTION

I have discovered that the normal rate and character of human hair growth, including male beard hair growth, can be altered by the topical application of compounds inhibiting the activity of ornithine decarboxylase. By the proper selection of ODC inhibitor and its mode of use, unwanted interference with other bodily processes can be minimized or avoided.

In employing the topical application of ODC inhibitors in alteriang the rate and character of hair growth, one may use a variety of ODC inhibitors either alone or in combination with 5-alpha-reductase inhibitors and/or cytoplasmic receptor-binding agents. Among the ODC inhibitors which may be employed are those described in U.S. Pat. Nos. 4,201,788; 4,413,141; and 4,421,768. The preferred compounds include 2(difluoromethyl)-2,5-diaminopentanoic acid; alpha-ethynyl ornithine; 6-heptyne-2,5-diamine; and 2-methyl-6-heptyne diamine.

In choosing ODC inhibitors for use in the practice of our invention, it is important to avoid those known to have secondary pharmacological effects such as 5-hexyne-1,4-diamine, which is known to bring about increases in brain 4-aminobutyric acid levels by a transformation catalyzed by mitochodrial monoamine oxidase. To minimize the risk of alteration of other bodily functions through systemic action, I prefer to apply the ODC inhibitors in compositions such that the level of application will range from about 1 to about 2000 micrograms of active material per square centimeter of skin. I prefer compositions which will result in the application of about 50 to about 500 micrograms per square centimeter.

Where, in the preferred practice of the invention, compositions are applied which contain in addition to an ODC inhibitor a 5-alpha-reductase inhibitor and/or a cytoplasmic binding agent, the concentration and level of application of these latter materials in formulated compositions should be such that from about 1 to about 1000 micrograms of active material per square centimeter of skin will be applied. I prefer compositions which will result in the application of about 10 to about 500 micrograms of 5-alpha-reductase inhibitor and/or cytoplasmic binding agent per square centimeter.

Among the 5-alpha-reductase inhibitors which may be employed are progesterone; (5, 20-R)-4-diazo-21-hydroxy-20-methyl pregnan-3-one; (4R)-5-10-seco-19-Norpregna4,5-diene-3,10,20 trione; 4-androstene-3-one-17-carboxylic acid, and its methyl ester; 17-β-N,N-diethylcarbamoyl-9-methyl4-aza-5α-androstane-3-one; 11-α-OH-progesterone; 17-α-OH-progesterone; and 20-α-OH-progesterone. For minimum alteration of other androgen-mediated bodily functions through systemic action, we prefer to use progesterone or 4-androstene-3-one-17-carboxylic acid.

Among the cytoplasmic receptor-binding agents, which may be employed, are cyproterone acetate, chlormadinone acetate, 17-alpha-propyltestosterone, 17-alpha-allyltestosterone, α-α-α-trifluoro-2-methyl-4'-nitro-m-propionotoluidide; 6α-bromo-17β-hydroxy-17α-methyl-4-oxa-5α-androstane-3-one; 17β-acetoxy-4α,5cyclo-A-homo-B-nor-5α-androst-1-ene-3one; and spironolactone. For minimal alteration of other androgen-mediated bodily functions through systemic action, we prefer to use 17-alpha-propyltestosterone or 17-alpha-allyltestosterone.

An experiment was conducted to demonstrate the inhibition of androgen-mediated hair growth in male hamsters following the topical application of 2(difluoromethyl)-2,5-diaminopentanoic acid to directly inhibit ODC. Five hundred micrograms of the compound in ten microliters of 70% ethanol was applied topically for 21 consecutive days. Hair mass changes were determined by comparing the regrowth of hair during the final ten days of treatment. Flank organ ODC activity was found to be reduced to levels found in hamsters castrated for 21 days. Furthermore, the magnitude of hair mass inhibition in the hamsters treated with the ODC inhibitor (60%) approached that observed in 21-day castrated hamsters (78%).

Additional experiments were conducted to test topical regimens composed of a combination of 2(difluoromethyl)-2,5-diaminopentanoic acid along with antiandrogens. Summarized below in Tables I and II are the results of two experiments comparing the efficacy of several compositions in reducing the flank organ hair mass in adult intact male hamsters. In each case, hamsters were treated for 15 days (Monday-Friday) during a 21-day interval. Flank organ hairs were epilated on the first day of treatment and re-epilated on the sixth day of treatment. The mass of flank organ hair represents the regrowth during the final 14 days of the 21-day interval. The results for percent inhibition shown below are based upon comparisons between the hair mass values of hairs harvested from treated flank organs of experimental animals and those obtained from vehicle-treated control animals.

TABLE I

| Compound(s) | Rate of Application in Micrograms Per Square Centimeter | % Inhibition |
| --- | --- | --- |
| Progesterone | 1000 | 50 |
| 2(difluoromethyl)-2,5-diaminopentanoic acid | 500 | 46 |
| Mixture of: | | |
| Progesterone and | 1000 | |
| (2(difluoromethyl)-2,5-diaminopentanoic acid | 500 | 66 |

TABLE II

| Compound(s) | Rate of Application in Micrograms Per Square Centimeter | % Inhibition |
| --- | --- | --- |
| Chloromadinone acetate | 500 | 41 |

TABLE II-continued

| Compound(s) | Rate of Application in Micrograms Per Square Centimeter | % Inhibition |
| --- | --- | --- |
| 2(difluoromethyl)-2,5-diaminopentanoic acid | 500 | 41 |
| Mixture of: | | |
| Chloromadinone and | 500 | |
| 2(difluoromethyl)-2,5-diaminopentanoic acid | 500 | 66 |

The above results reveal the improved efficacy of topical regimens composed of the combination of an ODC inhibitor and an anti-androgen with the combination regimens inhibiting hair mass to a greater extent than that achieved by single compound regimens.

A similar series of experiments was conducted to compare the effect of a variety of compositions with the following result.

TABLE III

| Treatment Group | Rate of Application & Micrograms per Square Centimeter | Flank Organ Hair Mass Untreated | Flank Organ Hair Mass Treated | % Inhibition |
| --- | --- | --- | --- | --- |
| Controls | — | 2.62 | 2.68 | — |
| Castrates | — | 0.95 | 0.97 | — |
| 2(difluoromethyl)-2,5-diaminopentanoic acid | 5 | 3.26 | 3.20 | 2 |
| 2(difluoromethyl)-2,5-diaminopentanoic acid | 50 | 3.05 | 2.85 | 7 |
| 2(difluoromethyl)-2,5-diaminopentanoic acid | 250 | 3.00 | 2.29 | 24 |
| 2(difluoromethyl)-2,5-diaminopentanoic acid | 500 | 2.71 | 1.81 | 33 |
| Mixture of: | | | | |
| 2(difluoromethyl)-2,5-diaminopentanoic acid + 17-alpha-allyltestosterone | 500 / 20 | 2.86 | 1.45 | 49 |
| Mixture of: | | | | |
| 2(difluoromethyl)-2,5-diaminopentanoic acid + Progesterone | 500 / 400 | 2.31 | 1.33 | 42 |
| Mixture of: | | | | |
| 2(difluoromethyl)-2,5-diaminopentanoic acid + Progesterone + 17-alpha-allyltestosterone | 500 / 400 / 20 | 2.89 | 1.14 | 61 |

In formulating the compositions to be applied topically in the practice of this invention, any dermatologically acceptable base or carrier may be employed. Care should be taken, however, to use a base or carrier which will provide uniform localized absorption of the active principles without significant systemic absorption. The art practiced in the formulation of skin creams for cosmetic purposes may usefully be employed in the formulation of compositions used in the practice of this invention. For example, many derivatives of lanolin are known to have excellent emulsifying properties and may be used to facilitate the formulation of emulsions having critical stability requirements. Lanolin has also been thought to aid in the absorption of active materials into the skin. While the active materials may be incorporated in a variety of cosmetic-based materials such as simple solutions, creams, suspensions, gels and the like, water-in-oil type cream emulsions may offer advantages in that the continuous oil phase provides direct contact with the lipids of the skin to provide a route for slow continuous absorption of the active principles.

In formulating the compositions of this invention, it is possible to include as little as 0.01% or as much as 20% by weight of ODC inhibitor. We prefer to use from 0.1% to 2.5% by weight. In formulating compositions containing in addition, 5-alpha-reductase inhibitors and/or cytoplasmic receptor-binding agents, it is possible to use from 0.01% to 10% by weight of these materials. We prefer, however, to use from 0.1% to 2.5% by weight.

In using the ODC inhibitor-containing compositions described herein in reducing the rate and altering the character of hair growth including beard hair growth, sufficient quantity of the composition is rubbed into the hirsute area of the skin preferably on a daily basis to provide the level of application discussed above. The maximum rate of change which will be achieved will vary from individual to individual.

The following examples are illustrative of compositions to be used in the practice of the invention but are not to be construed as limiting.

EXAMPLE 1

Skin Lotion

| Ingredients | Weight % |
| --- | --- |
| 2-(difluoromethyl)-2,5-diaminopentanoic acid | 2.0 |
| Progesterone | 2.2 |
| Cetyl Alcohol | 4.0 |
| Mineral Oil | 4.0 |
| Isopropyl Myristate | 1.0 |
| Dimethicone | 1.0 |
| Lanolin Alcohol | 0.5 |
| Glycerol monostearate | 1.0 |
| Sodium lactate (60% aq. soln.) | 1.4 |
| Dimethyl diammonium chloride (75% active)-Arquad 2HT75 | 2.0 |
| Propylene glycol | 3.0 |
| Methyl paraben | 0.2 |
| Propyl paraben | 0.1 |
| Titanium dioxide | 0.1 |
| Perfume | 0.1 |
| Water | 75.4 |

Procedure:

Deionized water and propylene glycol are heated to 70° C. Methyl paraben is added under high sheer agitation. In another container combine emollient oils, emulsifier, prewarmed dimethyl diammonium chloride, active ingredients and propyl paraben. Heat and maintain 70° C. with moderate agitation for 30 minutes. Add the water phase to the oil phase and agitate moderately. Add titanium dioxide and mix for 60 minutes. Cool batch slowly to 55° C., add the sodium lactate (60%) and continue to cool slowly with agitation to room temperature.

EXAMPLE 2

Cream Emulsion

| Concentrate | % w/w |
| --- | --- |
| A. 2-(difluoromethyl)-2,5- | 2.2 |
| 17-alpha-allyltestosterone | 1.5 |
| Stearic acid xxx | 7.6 |
| Amerchol L-101 | 5.0 |
| Modulon | 2.0 |
| Cetyl alcohol | 3.0 |
| Propyl Parasept | 0.1 |
| B. Glycerin | 4.0 |
| Methyl Paraben | 0.15 |
| Water | 74.45 |

Procedure:

Combine (A) ingredients and heat to 70° C. Combine (B) ingredients separately and heat to 72° C. Add (B) to (A) with rapid stirring, then cool to room temperature.

EXAMPLE 3

Aerosol Spray

| Concentrate | % w/w |
| --- | --- |
| A. Magnesium aluminum silicate (Veegum K) | 1.5 |
| Propylene glycol | 3.0 |
| Water | 86.0 |
| B. 2-methyl-6-heptyne diamine | 2.2 |
| Diethylene glycol mono-stearate s.e. | 3.0 |
| Silicone 556 Fluid | 1.0 |
| Cetyl alcohol | 0.5 |
| Acetylated lanolin alcohols | 2.0 |
| Preservative | 0.2 |

Procedure:

Add the Veegum to water slowly with rapid agitation, until smooth. Add remaining (A) ingredients and heat to 80° C. Combine (B) ingredients and heat to 75° C. Add (A) to (B) with mixing and cool to room temperature. Package as an aerosol by combining 90 parts of concentrate with 10 parts of hydrocarbon propellent A-46.

EXAMPLE 4

Aerosol Foam

| Concentrate | % w/w |
| --- | --- |
| A. Progesterone | 2.0 |
| 6-Heptyne-2,5 diamine | 0.2 |
| Cetyl alcohol | 5.2 |
| Polyoxyethylene (401 stearate (MYRJ52)) | 3.0 |
| B. Propylene glycol | 4.0 |
| Water | 85.4 |

| Concentrate | % w/w |
| --- | --- |
| Preservative | 0.2 |

Procedure:

Combine (A) ingredients and heat to 70° C. Combine (B) ingredients separately and heat to 72° C. Add (B) to (A) with mixing and cool to room temperature. Package as aerosol using a ratio of 7 parts hydrogen propellent A-31 to 93 parts of concentrate.

Example 5

Alcohol Solution

| Concentrate | % w/w |
| --- | --- |
| 2-(difluoromethyl)-2,5-diamino-pentanoic acid | 2.2 |
| Progesterone | 1.0 |
| 17-alpha-allyltestosterone | 1.0 |
| Propylene glycol | 4.0 |
| Dimethicone | 1.0 |
| SDA-40 Alcohol | 90.8 |

Procedure:

Combine ingredients with mixing and package.

I claim:

1. The process of reducing the rate and altering the character of human hair growth which comprises the step of applying to the skin a composition containing an ornithine decarboxylase inhibitor.

2. The process as described in claim 1 in which said ornithine decarboxylase inhibitor is selected from the group including 2-(difluoromethyl)-2,5-diaminopentanoic acid; alpha-ethynyl ornithine; 6-heptyne-2,5-diamine; and 2-methyl-6-heptyne diamine.

3. The process as described in claim 2 resulting in the application of from about 1 to about 2000 micrograms of said ornithine decarboxylase inhibitor per square centimeter of skin.

4. The process as described in claim 2 resulting in the application of from about 50 to about 500 micrograms of said ornithine decarboxylase inhibitor per square centimeter of skin.

5. The process as described in claim 1 and in which said composition contains in addition an anti-androgen material selected from the group consisting of 5-alpha-reductase inhibitors and cytoplasmic androgen receptor-binding agents.

6. The process as described in claim 5 in which said anti-androgen is selected from the group consisting of progesterone; (5α, 20-R)-4-diazo-21-hydroxy-20-methyl pregnan-3-one; (4R)-5-10-seco-19-Norpregna4,5-diene-3,10,20 trione; 4-androstene-3-one-17-carboxylic acid, and its methyl ester; 17-β-N,N-diethylcarbamoyl-9-methyl4-aza-5α-androstane-3-one; 11-α-OH-progesterone; 17-α-OH-progesterone; and 20-α-OH-progesterone; cyproterone acetate; chlormadinone acetate; 17-alpha-propyltestosterone; 17-alpha-allyltestosterone; α-α-α-trifluoro-2-methyl-4'-nitro-m-propionotoluidide; 6α-bromo-17β-hydroxy-17α-methyl-4-oxa-5α-androstane-3-one; 17β-acetoxy-4α,5cyclo-A-homo-B-nor-5α-androst-1-ene-3one; and spironolactone.

7. The process as described in claim 6 in which about 1 to about 500 micrograms of said anti-androgen is applied per square centimeter of skin.

8. A topical composition for reducing the rate and altering the character of human hair growth comprising from about 0.01 to about 20% by weight of an ornithine decarboxylase inhibitor in combination with from about 0.01 to 10% by weight of an anti-androgen selected from the group consisting of 5-alpha-reductase inhibitors and cytoplasmic androgen receptor-binding agents.

9. A composition as described in claim 8 in which said ornithine decarboxylase inhibitor is selected from the group including 2-(difluoromethyl)-2,5-diaminopentanoic acid; alpha-ethynyl ornithine; 6-heptyne-2,5-diamine; and 2-methyl-6-heptyne diamine and said anti-androgen is selected from the group including progesterone; (5α, 20-R)-4-diazo-21-hydroxy-20-methyl pregnan-3-one; (4R)-5-10-seco-19-Norpregna4,5-diene-3,10,20 trione; 4-androstene-3-one-17-carboxylic acid, and its methyl ester; 17-β-N,N-diethylcarbamoyl-9-methyl4-aza-5α-androstane-3-one; 11-α-OH-progesterone; 17-α-OH-progesterone; and 20-α-OH-progesterone; cyproterone acetate; chlormadinone acetate; 17-alpha-propyltestosterone; 17-alpha-allyltestosterone; α-α-α-trifluoro-2-methyl-4'-nitro-m-propionotoluidide; 6α-bromo-17β-hydroxy-17α-methyl-4-oxa-5α-androstane-3-one; 17β-acetoxy-4α,5cyclo-A-homo-B-nor-5α-androst-1-ene-3one; and spironolactone.

* * * * *